US00PP24460P2

(12) United States Plant Patent
Falcetti-Arnold

(10) Patent No.: US PP24,460 P2
(45) Date of Patent: May 13, 2014

(54) ***HELENIUM* PLANT NAMED 'SHORT 'N' SASSY'**

(50) Latin Name: *Helenium autumnale*
Varietal Denomination: Short n Sassy

(75) Inventor: Gina M. Falcetti-Arnold, Sedro Woolley, WA (US)

(73) Assignee: Skagit Gardens Inc., Mount Vernon, WA (US)

( * ) Notice: Subject to any disclaimer, the term of this patent is extended or adjusted under 35 U.S.C. 154(b) by 91 days.

(21) Appl. No.: 13/573,321

(22) Filed: Sep. 11, 2012

(51) Int. Cl.
*A01H 5/00* (2006.01)

(52) U.S. Cl.
USPC ..... Plt./435

(58) Field of Classification Search
USPC ..... Plt./435
See application file for complete search history.

*Primary Examiner* — Annette Para
(74) *Attorney, Agent, or Firm* — Penny J. Aguirre

(57) ABSTRACT

A new cultivar of *Helenium*, 'Short 'n' Sassy', characterized by its dwarf plant habit; reaching 45 to 56 cm in height, its early commencement of bloom with new blooming stems continuously produced that rise above the older spent blooms and its inflorescences with ray florets that are a blend of yellow and red in color creating a yellow and orange effect.

2 Drawing Sheets

Botanical classification: *Helenium autumnale.*
Variety denomination: 'Short 'n' Sassy'.

BACKGROUND OF THE INVENTION

The present invention relates to a new and distinct cultivar of *Helenium autumnale* and will be referred to hereafter by its cultivar name, 'Short 'n' Sassy'. 'Short 'n' Sassy' represents a new *Helenium*, an herbaceous perennial grown for landscape use.

The Inventor discovered the new *Helenium* as a naturally occurring whole plant mutation in summer of 2009 in a garden in Mount Vernon, Wash. The parentage is unknown.

Asexual reproduction of the new cultivar was first accomplished by stem cuttings by the Inventor in Mount Vernon, Wash. in August of 2009. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Short 'n' Sassy' from other cultivars of *Helenium* known to the Inventor.

1. 'Short 'n' Sassy' exhibits a dwarf plant habit; reaching 45 to 56 cm in height.
2. 'Short 'n' Sassy' blooms 2 to 3 weeks earlier than is typical of most cultivars of *Helenium autumnale.*
3. 'Short 'n' Sassy' continues to produce new bloom stalks that rise above the older spent blooms; a characteristic not typically observed in cultivars of *Helenium autumnale.*
4. 'Short 'n' Sassy' exhibits inflorescences with ray florets that are a blend of yellow, and red creating a yellow and orange effect.

'Short 'n' Sassy' can be most closely compared to the cultivars 'Mardi Gras' (U.S. Plant Pat. No. 15,124) and 'Pipsqueak' (not patented). 'Mardi Gras' is similar to 'Short 'n' Sassy' in having flowers that are similar in color. 'Mardi Gras' differs from 'Short 'n' Sassy' in being about twice as tall and in blooming 2 to 3 weeks later in the growing season. 'Pipsqueak' is similar to 'Short 'n' Sassy' in having a dwarf plant habit. 'Pipsqueak' differs from 'Short 'n' Sassy' in having ray florets that are solid yellow in color and in blooming later in the season.

BRIEF DESCRIPTION OF THE DRAWING

The accompanying colored photographs illustrate the overall appearance and distinct characteristics of the new *Helenium*. The plants in the accompanying photographs were taken of a one year-old plant of 'Short 'n' Sassy' as grown in a two-gallon container in Mount Vernon, Wash.

The photograph in FIG. 1 depicts a plant of 'Short 'n' Sassy' in bloom.

Figure 1:
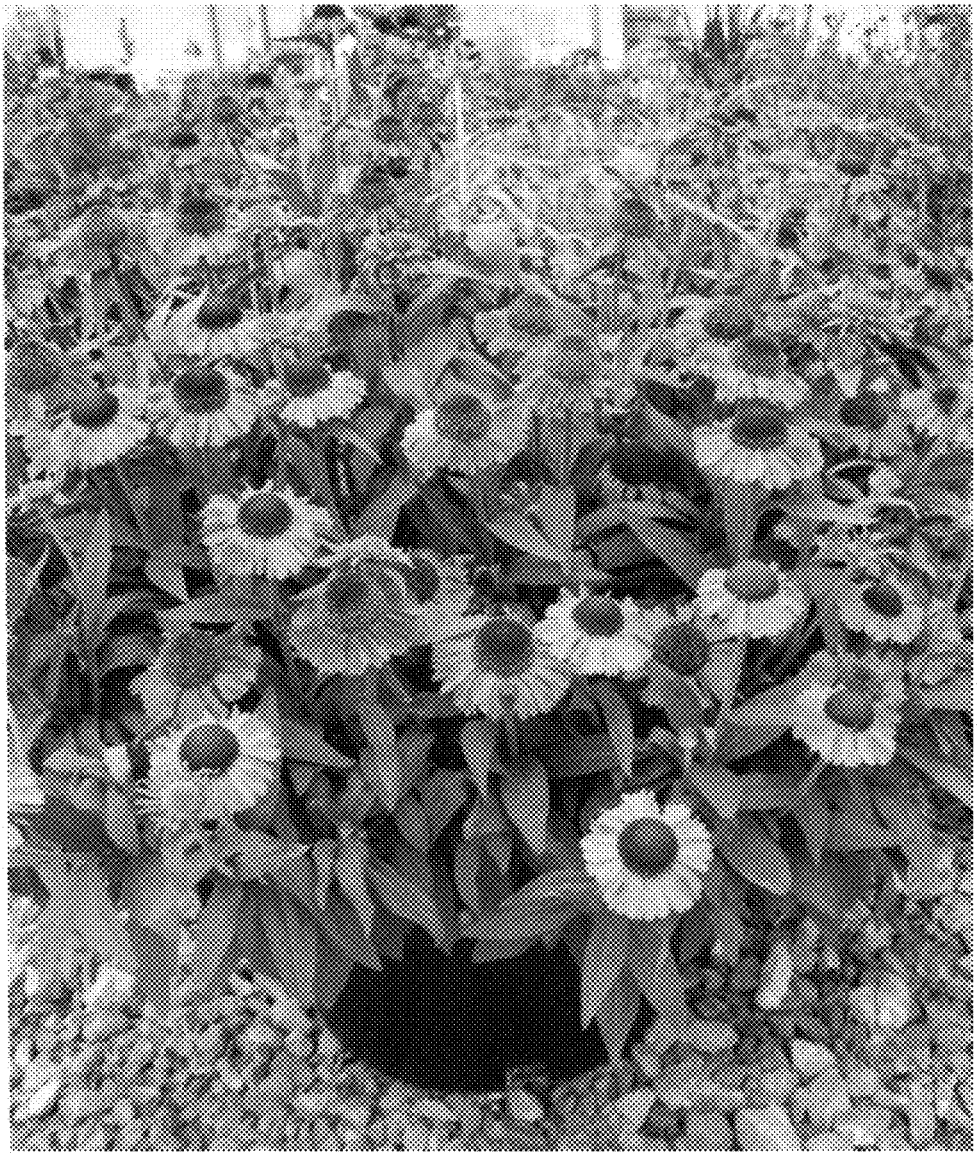
Figure 2:
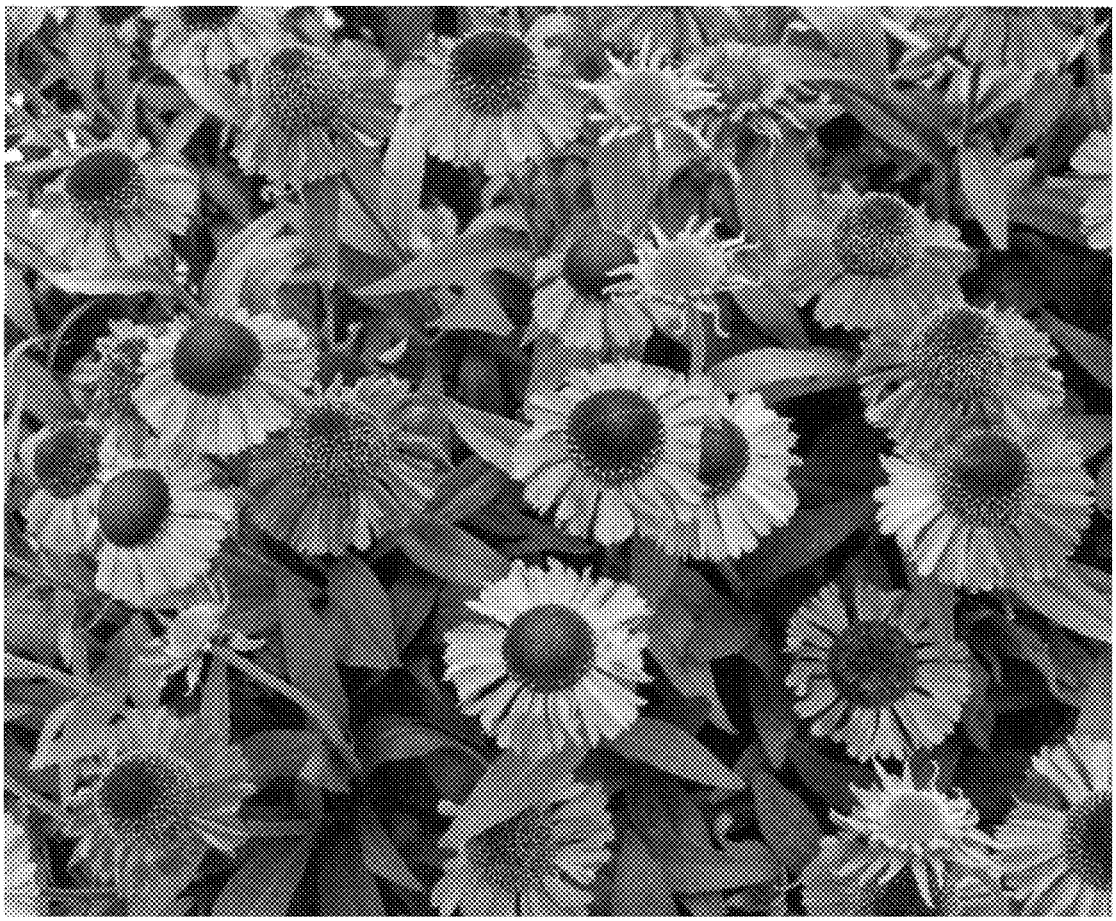

The photograph in FIG. 2 shows a close-up of the inflorescences of 'Short 'n' Sassy'. The colors in the photograph may differ slightly from the color values cited in the detailed botanical description, which accurately describe the colors of the new *Helenium.*

BOTANICAL DESCRIPTION OF THE PLANT

The following is a detailed description of one-year-old plants of the new cultivar as grown in two-gallon containers in Mount Vernon, Wash. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Commences bloom early in mid summer and blooms for 8 to 10 weeks in Mount Vernon, Wash.

*Plant habit*.—Herbaceous perennial, clump forming, dwarf, upright mound.

*Height and spread*.—Reaches 45 to 56 cm in height and about 61 cm in spread.

*Hardiness*.—U.S.D.A. Zones 4 to 8.

*Diseases and pests*.—No susceptibility or resistance to diseases or pests has been observed.

*Root description*.—Fibrous.

*Propagation*.—Stem cuttings.

*Growth rate*.—Moderate.

Stem description:

*Shape*.—Slightly oval.

*Stem color*.—Main stem; a blend of 144A with ridges of leaf scars near base N199B, lateral stems; a blend of 144A with leafy edges from excurrent leaves 144A.

*Stem size*.—Main stem; an average of 15 cm in length and 4.5 mm in diameter, lateral branches; and an average of 10 cm in length and 2.5 mm in width.

*Stem surface*.—Main stem; glabrous, semi glossy with lower region ridged with leaf scars from excurrent leaves, lateral stems; covered with base of leaves with leaf edges extending about 1 mm outward from stem; puberulent.

*Stem number and branching*.—An average of 10 main stems with an average of 5 lateral stems per main stems.

*Internode length*.—An average of 5 mm with branching commencing an average of 15 cm from base of main stems.

Foliage description:

*Leaf shape*.—Oblanceolate.

*Leaf division*.—Simple.

*Leaf base*.—Excurrent to stem with blade truncate to stem.

*Leaf apex*.—Narrowly acute.

*Leaf venation*.—Pinnate, only mid rib on upper and lower surfaces are conspicuous, color of midrib upper and lower surface; 144D.

*Leaf margins*.—Entire.

*Leaf attachment*.—Excurrent.

*Leaf arrangement*.—Alternate.

*Leaf size*.—Matures to an average of 8 cm in length and 2 cm in width with excurrent portion an average of 1.5 cm in next lower node.

*Leaf internode length*.—An average of 4 mm.

*Leaf color*.—Newly formed and mature, upper surface; a blend of 147A and 146A, newly formed and mature lower surface; a blend of 146A and 147B.

*Leaf surface*.—Dull and finely puberulent on upper and lower surface.

*Stipules*.—Present at some junctions of the leave blades, same characteristics as stem leaves and an average of 1.5 cm in length and 5 mm in width.

Flower description:

*Type*.—Capitulum, heterogamous with ray florets around the head margin and disk florets in the center, forming a radiant head.

*Capitulum number*.—An average of 5 capitulums per main stems present on the terminals of the lateral branches with new blooming stems produced after the main flush that rise above the spent blooms.

*Lastingness of inflorescence*.—About 10 days until senescence of ray flowers, disk flowers are persistent.

*Capitulum size*.—About 2 cm in depth and 4 cm in diameter, disk size is about 1.2 mm in depth and 1.8 cm in diameter.

*Fragrance*.—None detected.

*Involucral bracts or phyllary*.—About 22 arranged in 3 overlapping rows, up to 1.2 cm in length and 3 mm in width, fused at base, narrowly acute apex, lanceolate in shape, 137A to 137B in color, entire ciliate margin and puberulent on both surfaces, held horizontal on buds and becomes reflexed when capitulum is fully open.

*Buds*.—Globose and becomes disk-shaped, up to 2 cm in diameter and 7 mm in height, phyllary are 144C in color, ray florets are 14B with tinge of 34B, disk N144C and tinged with 59A near edges.

*Peduncle*.—Strong, held upright to stem, an average of 2 cm in length and an average of 2 mm in diameter, 146B in color, pubescent surface.

*Ray florets* (*pistillate*).—About 12, obdeltoid in shape, vertical ridges on both surfaces, about 1.6 cm in length and 1.2 cm in width, emarginated apex, attenuate base, entire margin except apex, glabrous on upper and lower surface, initially held slightly upright and become horizontal, then downward as they mature, color of upper surface when opening and fully open; a blend of 9A and 34B, color of lower surface when opening and fully open lower surface; a blend of 9A and N34A with a few markings of 138A.

*Disk florets* (*bisexual*).—Numerous, about 300, tubular in shape, arranged spirally on a globose receptacle to form a sphere, overall collective color 79A, florets; about 4.5 mm in length and 1.5 mm in width, petals (5) are fused into tube about 4 mm in length and 1.5 mm in width and 79A at apex and 145C in color near base, translucent.

Reproductive organs:

*Gynoecium*.—Pistil; 1, present on ray and disk florets, 4.5 mm in length, style; 65 mm in length, 145C in color, surrounded by stamens, stigma; bifid, each arm is reflexed, about 1 mm in length and 17A in color, ovary; inferior, 1 mm in depth and pubescent, 145D in color.

*Androcoecium*.—Stamens; 5, fused, form a cylinder around style, about 2 mm in length and 0.5 mm in width, filaments are 145C in color, stamens about N199B in color, pollen was not visible.

*Seed*.—Fertile seed development has not been observed.

It is claimed:

1. A new and distinct cultivar of *Helenium* plant named 'Short 'n' Sassy' substantially as herein illustrated and described.

* * * * *